US009216949B2

(12) United States Patent
Tan et al.

(10) Patent No.: US 9,216,949 B2
(45) Date of Patent: Dec. 22, 2015

(54) KETOXIME- AND AMIDE-FUNCTIONALIZED NANOMATERIALS

(71) Applicant: The United States of America as Represented by the Secretary of the Air Force, Washington, DC (US)

(72) Inventors: Loon-Seng Tan, Centerville, OH (US); David Huabin Wang, Beavercreek, OH (US)

(73) Assignee: THE UNITED STATES OF AMERICA, AS REPRESENTED BY THE SECRETARY OF THE AIR FORCE, Washington, DC (US)

( * ) Notice: Subject to any disclaimer, the term of this patent is extended or adjusted under 35 U.S.C. 154(b) by 108 days.

(21) Appl. No.: 13/933,421

(22) Filed: Jul. 2, 2013

(65) Prior Publication Data
US 2015/0011794 A1 Jan. 8, 2015

(51) Int. Cl.
*C07C 249/08* (2006.01)
*C07C 231/10* (2006.01)
*C09C 3/08* (2006.01)

(52) U.S. Cl.
CPC ............. *C07C 249/08* (2013.01); *C07C 231/10* (2013.01); *C09C 3/08* (2013.01)

(58) Field of Classification Search
None
See application file for complete search history.

(56) References Cited

U.S. PATENT DOCUMENTS

| | | | |
|---|---|---|---|
| 5,521,277 | A | 5/1996 | Tan et al. |
| 5,534,613 | A | 7/1996 | Tan et al. |
| 5,633,337 | A | 5/1997 | Tan et al. |
| 6,300,502 | B1 | 10/2001 | Kannan et al. |
| 6,538,098 | B1 | 3/2003 | Goldfinger |
| 6,555,682 | B1 | 4/2003 | Kannan et al. |
| 6,680,016 | B2 | 1/2004 | Wang et al. |
| 6,696,142 | B2 | 2/2004 | Baer et al. |
| 6,730,793 | B1 | 5/2004 | Kannan et al. |
| 6,849,707 | B1 | 2/2005 | Baek et al. |
| 6,867,304 | B1 | 3/2005 | Tan et al. |
| 6,974,857 | B1 | 12/2005 | Baek et al. |
| 7,005,550 | B1 | 2/2006 | Tan et al. |
| 7,026,432 | B2 | 4/2006 | Charati et al. |
| 7,067,674 | B1 | 6/2006 | Kannan et al. |
| 7,319,151 | B1 | 1/2008 | Tan et al. |
| 7,807,127 | B1 | 10/2010 | Forohar et al. |
| 7,960,471 | B1 | 6/2011 | Tan et al. |
| 8,173,763 | B1 | 5/2012 | Tan et al. |
| 8,318,888 | B1 | 11/2012 | Tan et al. |
| 8,580,958 | B1 | 11/2013 | Tan et al. |
| 2007/0052350 | A1 | 3/2007 | Su et al. |
| 2010/0102761 | A1 | 4/2010 | Von Malm et al. |
| 2011/0108813 | A1 | 5/2011 | Kohiro et al. |

OTHER PUBLICATIONS

Loon-Seng Tan et al., "Synthesis and Characterization of a Novel Film-Forming, Two-Photon Absorbing Benzobisthiazole Polymer and Related Model Compound", Abstract for poster presentation at "9th International Symposium on Functional Pi-Electron Systems" Conference, Georgia Institute of Technology, Atlanta, GA, May 23-28, 2010.
Jenekhe, Samson A.; Osaheni, John A.; Meth, Jeffrey S.; Vanherzeele, Herman, "Nonlinear optical properties of poly (p-phenylenebenzobisoxazole)", Chemistry of Materials, (1992) vol. 4, Issue 3, pp. 683-687.
Tan, Loon-Seng; Srinivasan, K. R.; Bai, Shih Jung; Spry, Robert J. "New aromatic benzazole polymers II: synthesis and conductivity of benzobisthiazole-co-polymers incorporated with 4-N,N-dimethylaminotriphenylamine groups", Journal of Polymer Science, Part A: Polymer Chemistry (1998), 36(5), 713-724.
Kevin D. Belfield, Sheng Yao, Alma R. Morales, Joel M. Hales, David J. Hagan, Eric W. Van Stryland, Victor M. Chapela, Judith Percino, "Synthesis and characterization of novel rigid two-photon absorbing polymers", Polymers for Advanced Technology (2005) 16: 150-155.
Tan, Loon-Seng; Srinivasan, K. R.; Bai, Shih Jung, "New aromatic benzazole polymers I: Benzobisthiazole and benzobisoxazole polymers with main-chain triarylamino units", Journal of Polymer Science, Part A: Polymer Chemistry (1997), 35(10), 1909-1924.
Kazuo Naga, Katsumasa Iwaya, Ryohei Kaneko, "Condensation of 1,4-cyclohexanediones and secondary aromatic amines II: N-phenylation of diarylamines", Bulletin of the Chemical Society of Japan (1986), 59(3), 803-807.
United States Patent and Trademark Office, Non-Final Office Action in U.S. Appl. No. 14/047,640, mailed Dec. 16, 2013, 14 pages total.
United States Patent and Trademark Office, Final Office Action in U.S. Appl. No. 13/239,606, mailed Jul. 9, 2013, 9 pages.
United States Patent and Trademark Office, Non-Final Office Action in U.S. Appl. No. 13/632,195, mailed Oct. 18, 2013, 10 pages total.
United States Patent and Trademark Office, Final Office Action received in U.S. Appl. No. 14/047,460, mailed Jun. 18, 2014.
H. Peng et al., "Green and highly efficient functionalization of carbon nanotubes by combination of 1,3-dipolar cycloaddition and Curtius rearrangement reactions," Chinese J. Chem., vol. 28 (2010) 1223-1228.
L-S. Tan et al., Unpublished U.S. Appl. No. 10/963,469, filed Oct. 12, 2004, 15 pages total.
J. R. Smith et al., "Space durable polymer/carbon nanotube films for electrostatic charge mitigation," Polymer, vol. 45 (2004) 825-835.
H. Kong et al., "Controlled functionalization of multiwalled carbon nanotubes by in situ atom transfer radical polymerizations," JACS., vol. 126 (2004) 412-413.
J.-B Baek et al., "Improvded syntheses of Poly(oxy-1,3-phenylenecarbonyl-1,4-phenylene) and related poly(ether-keontes) using polyphosphoric acid/P2O5 as polymerization medium," Polymer, vol. 44 (2003) 4135-4137.
J. L. Bahr et al., "Covalent chemistry of single-wall carbon nanotubes," J. Mater. Chem., vol. 12 (2002) 1952-1958.

(Continued)

*Primary Examiner* — Rosalynd Keys
*Assistant Examiner* — Jennifer C Sawyer
(74) *Attorney, Agent, or Firm* — AFMCLO/JAZ; James P. Carey

(57) ABSTRACT

Ketoxime- and amide-functionalized nanomaterials. The nanomaterials including a nanomaterial comprising a carbon nanotube or a carbon nanofiber. At least one ketoxime group coupled to a first location on the nanomaterial, and at least one amide group coupled to a second location on the nanomaterial.

15 Claims, 9 Drawing Sheets

(56) References Cited

OTHER PUBLICATIONS

K. A. Watson et al., "Polyimide/carbon nanotube composite films for potential space applications," Int'l SAMPE Tech. Conf., vol. 33 (2001) 1551-1560.

B. Maruyama et al., "Carbon nanotubes and nanofibers in composite materials," J. SAMPE., vol. 38, (2002) 59-70.

M.S.P. Shaffer et al., "Polystyrene granted multi-walled carbon nanotubes," Chem. Commun. (2002) 2074-2075.

C. Park et al., "Dispersion of single wall carbon nanotubes by in-situ polymerization under sonication," Chem. Phys. Lett., vol. 364 (2002) 303-308.

N. Tagmatarchis et al., "Sidewall functionalization of single-walled carbon nanotubes through electrophilic addition," Chem. Commun. (2002) 2010-2011.

United States Patent and Trademark Office, Non-Final Office Action in related U.S. Appl. No. 10/963,469, mailed Sep. 26, 2007, 7 pages total.

United States Patent and Trademark Office, Final Office Action in related U.S. Appl. No. 10/963,469, mailed Apr. 8, 2008, 9 pages total.

Y. Iwakura et al., "Syntheses of aromatic polyketones and aromatic polamides," J. Polymer Sci., vol. 6 (1968) 3345-3355.

United States Patent and Trademark Office, Advisory Action in related U.S. Appl. No. 10/963,469, mailed Jul. 2, 2008, 6 pages total.

A. Ambrosio et al., "Two-photon patterning of a polymer containing Y-shaped azochromophores," Appl. Phys. Lett., vol. 94 (2009) 011115-1 to 011115-3.

D-S Won et al., "Synthesis and nonlinear optical properties of a novel polyurethane containing cyanovinylthiophene with enhanced thermal stability of dipole alignment for electro-optic applications," Polym. Int., vol. 59 (2010) 162-168.

G. S. He et al., "Multiphoton absorbing materials: molecular designs, characterizations, and applications," Chem. Rev., vol. 108 (2008) 1245-1330.

G. S. He et al., "Degenerate two-photon-absorption spectral studies of highly two-photon active organic chromophores," J. Chem. Phys., vol. 120 (2004) 5275-5284.

J. E. Beecher et al., "Concurrent stabilization and imaging of a novel polymer for second harmonic generation via in situ photopolymerization," in Technical Report #14 (1994), 67 pages total.

J. E. Rogers et al., "Insight into the nonlinear absorbance of two related series of two-photon absorbing chromophores," J. Phys. Chem. A., vol. 111 (2007) 1899-1906.

M. J. Dalton et al., "Aromatic polyimides containing main-chain diphenylaminofluorene-benzothiazole motif: fluorescence quenching, two-photon properties, and exciplex formation in solid state," Macromol., vol. 44 (2011) A-M.

R. Kannan, "Twoard highly active two-photon absorbing liquids, synthesis and characterization of 1,3,5-triazine-based octupolar molecules," Chem. Mater., vol. 16 (2004) 183-194.

R Kannan, "Diphenylaminofluorene-based two-photon-absorbing chromophores with various pi-electron acceptors," Chem. Mater., vol. 13 (2001) 1896-1904.

S. J. Jhaveri et al., "Direct three-dimensional microfabrication of hydrogels via two-photon lithography in aqueous solution," Chem. Mater., vol. 21 (2009) 2003-2006.

United States Patent and Trademark Office, Non-Final Office Action in related U.S. Appl. No. 13/239,606, mailed Mar. 28, 2013, 9 pages total.

Z Yuxia et al., "Synthesis and characterization of a novel nonlinear optical polyurethane polymer," Eur. Poly. J., vol. 37 (2001) 445-449.

J-B. Baek et al., "Covalent modification of vapour-grown carbon nanofibers via direct Friedel-Crafts acylation in polyphosphoric acid," J. Mater. Chem., vol. 14 (2004) 2052-2056.

83.1 % yield 16.9 % yield

KETOXIME- AND AMIDE-FUNCTIONALIZED NANOMATERIALS

RIGHTS OF THE GOVERNMENT

The invention described herein may be manufactured and used by or for the Government of the United States for all governmental purposes without the payment of any royalty.

FIELD OF THE INVENTION

The present invention relates generally to nanomaterials and, more specifically, to grafted and functionalized carbon nanotubes and nanofibers.

BACKGROUND OF THE INVENTION

One-dimensional, carbon-based, nano-structured materials, which are formally derived from the rolling up of single or multiple graphene sheets into tubular structures, are generally divided into three categories (based on diameter dimensions): single-wall carbon nanotubes ("SWNT") having diameters ranging from 0.7 nm to 3 nm; multi-wall carbon nanotubes or CNT having diameters ranging from 2 nm to 20 nm; and carbon nanofibers ("CNF") having diameters ranging from 40 nm to 100 nm. The length of vapor grown carbon nanofibers ("VGCNF") may range from 30 μm to 100 μm. While the length of SWNT and CNT is difficult to determine because of a strong proclivity to aggregate or form ropes, the lengths of SWNTs and CNTs are generally considered to be two-orders of magnitude shorter than VGCNFs.

Carbon nanomaterials have captivated wide-spread attention in the advanced materials research community because of the predicted extraordinary thermal, mechanical, and electrical properties. To take advantage of their predicted mechanical properties, several studies have been performed on CNT or CNF and reported their reinforcement effects in various thermoplastics and thermoset matrices.

Great strides have been made in the functionalization of SWNT to impart solubility and processing options. Similar to fullerene derivatization chemistry, the general nature of chemical reactions utilized in conventional CNT functionalization are compatible with the electron-deficient character of the carbon nanotubes. This generalization is understandably applicable to the reaction chemistry involving the perfect graphene framework. However, defect sites, (for example, the pre-existing $sp^2$ C—H bonds), of these graphene-based nanomaterials may behave differently.

Graphene-based nanomaterials have such broad applications because of particular thermal, electrical, mechanical, and photonic properties. Therefore, graphene-based nanomaterials are actively investigated with respect to their structural reinforcement, energy/electron transport or storage capabilities, and interactions with electromagnetic waves.

The chemical medication of graphene-based surfaces and edges is usually quantitatively assessed by using the combination of thermogravimetric analysis ("TGA") and elemental analysis. Experimentally, under TGA conditions, organic functional groups are thermally degraded at temperatures well below the thermal degradation of carbon nanomaterials (much greater than 600° C.). Therefore, the total amount of the specific organic group in the original test sample can be estimated by the associated weight loss. Such estimation is referred to as degree of functionalization (DF or τ and expressed in terms of atom %). It follows that a rough, empirical formula for the functionalized carbon nanomaterial sample may be derived and elemental analysis based on this empirical formula is used for its confirmation. For example, when VGCNF is functionalized via a Friedel-Crafts acylation reaction, the DF for VGCNF is estimated to be 3 atom %, that is to say, on average for every 100 carbon atoms of a single nanofibers, there are 3 functional group grafted.

Therefore, it would be desirable to transfer one or more of these properties to polymeric matrices, for example, it is desirable to transfer such electrical, mechanical, and optical properties to bulk materials via the chemical modification of nanomaterial surfaces and edges to promote or enhance specific interactions or bonding strength between the matrix and the functionalized nanomaterial.

SUMMARY OF THE INVENTION

The present invention overcomes the foregoing problems and other shortcomings, drawbacks, and challenges of modifying nanomaterial surfaces for improving transfer of properties to bulk materials. While the invention will be described in connection with certain embodiments, it will be understood that the invention is not limited to these embodiments. To the contrary, this invention includes all alternatives, modifications, and equivalents as may be included within the spirit and scope of the present invention.

One embodiment of the present invention is directed to a functionalized nanomaterial, which includes a nanomaterial comprising a carbon nanotube or a carbon nanofiber. At least one ketoxime group is coupled to a first location on the nanomaterial, and at least one amide group is coupled to a second location on the nanomaterial.

Yet another embodiment of the present invention is directed to a method of synthesizing a ketoxime- and amide-functionalized nanomaterial. The method includes converting a keto-carbonyl group, which is coupled to the nanomaterial to an oxime group. The oxime group then undergoes a Beckmann Rearrangement to an amide group.

Other embodiments of the present invention are directed to a method of synthesizing a ketoxime- and amide-functionalized nanomaterial. The method includes grafting, with a Friedel-Crafts acylation, the keto-carbonyl group onto the nanomaterial. The keto-carbonyl group is converted to an oxime group and undergoes a Beckmann Rearrangement to an amide group.

Yet another embodiment of the present invention is directed to a functionalized nanomaterial of which the nanomaterial comprises a carbon nanotube or a carbon nanofiber. At least ketoxime group is coupled to the nanomaterial.

According to still another embodiment of the present invention, a functionalized nanomaterial includes a nanomaterial comprises a carbon nanotube or a carbon nanofiber. At least amide group is coupled to the nanomaterial.

Another embodiment of the present invention includes a functionalized nanomaterial having at least one external surface and at least one edge. The nanomaterial is a carbon nanotube or a carbon nanofiber. At least one primary amine group is coupled to the at least one external surface of the nanomaterial. At least one primary amine group is coupled to the at least one edge of the nanomaterial. At least one primary carboxylic acid group is coupled to the at least one external surface of the nanomaterial. And, at least one primary carboxylic acid group is coupled to the at least one edge of the nanomaterial.

Additional objects, advantages, and novel features of the invention will be set forth in part in the description which follows, and in part will become apparent to those skilled in the art upon examination of the following or may be leaned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Figure 1:
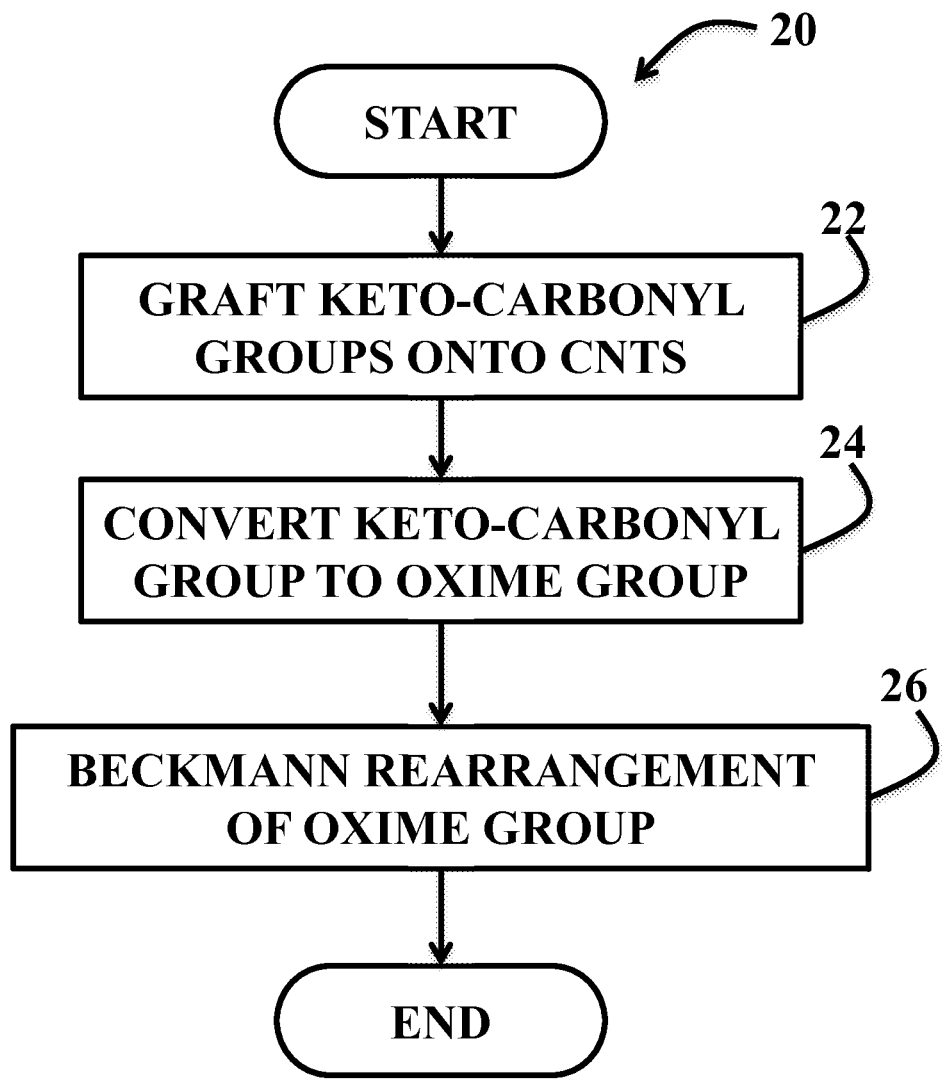
FIG. 1 is a flowchart illustrating a method of functionalizing CNTs according to one embodiment of the present invention.

Referring now to the figures, and in particular to FIG. 1, a flowchart 20 illustrating a method of synthesizing ketoxime- or amide-functionalized graphene-based nanomaterials according to one embodiment of the present invention are shown, respectively.

In Block 22 of FIG. 1, carbon nanotubes ("CNTs") are grafted with keto-carbonyl groups via Friedel-Crafts (F-C) acylation in optimized PPA/P$_2$O$_5$ using methods described in U.S. application Ser. No. 10/963,469, entitled NANOCOMPOSITES FROM IN-SITU POLYMERIZATION OF 3-PHENOXYBENZOIC ACID IN THE PRESENCE OF VAPOR-GROWN CARBON NANOFIBERS; U.S. application Ser. No. 12/233,423, entitled NANOCOMPOSITES FROM IN-SITU POLYMERIZATION OF 3-PHENOXY-BENZOIC ACID IN THE PRESENCE OF VAPOR-GROWN CARBON NANOFIBERS, and issued as U.S. Pat. No. 7,960,471 on Jun. 14, 2011; and U.S. application Ser. No. 12/079,083, entitled CARBON NANOFIBERS AND NANOTUBES GRAFTED WITH A HYPERBRANCHED POLY (ETHER-KETONE) AND ITS DERIVATIVES, and issued as U.S. Pat. No. 8,173,763 on May 8, 2012, the disclosure of each incorporated herein by reference, in its entirety. The surface keto-carbonyl group may then be then converted to an oxime group (Block 24) and followed by effecting a Beckmann rearrangement in sulfuric acid (FIG. 26).

Figure 2:
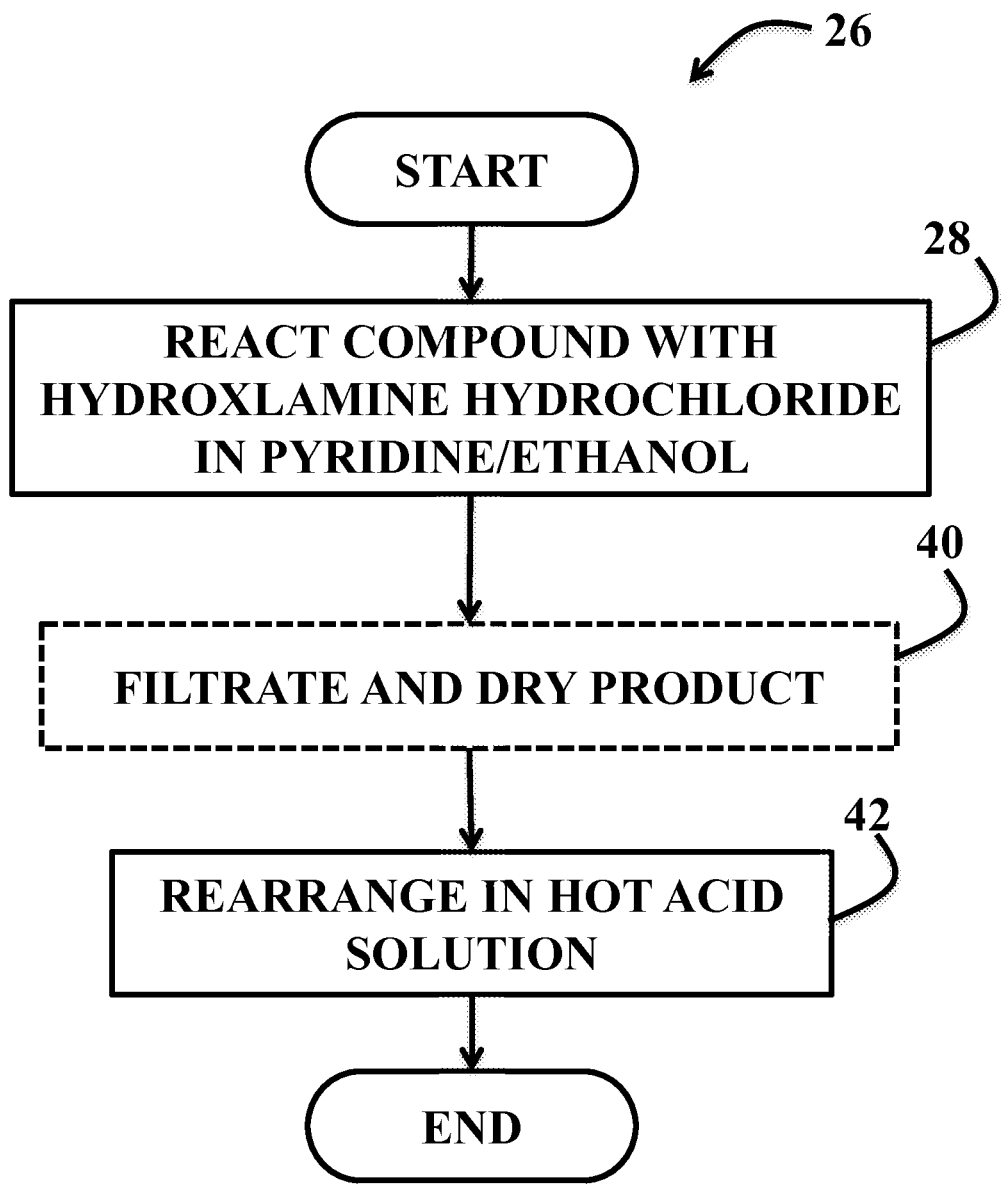
FIG. 2 is a flowchart illustrating a Beckmann rearrangement of an oxime group of the CNTs of FIG. 1.
Figure 3:
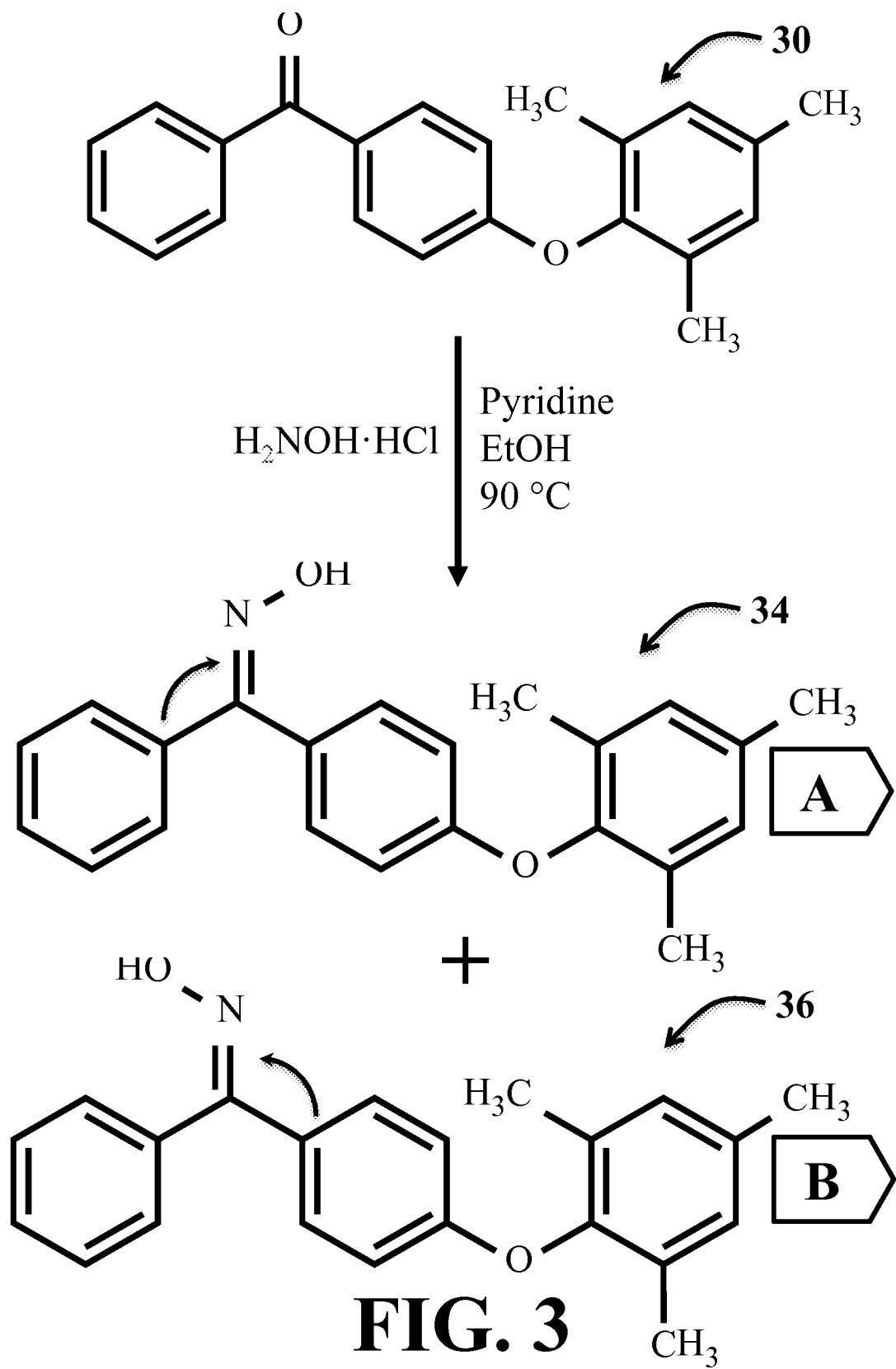
FIG. 3 is a schematic representation of a chemical reaction between a model compound 4-(2,4,6-trimethylphenoxy)benzophenone and hydroxylamine hydrochloride.
Figure 4:
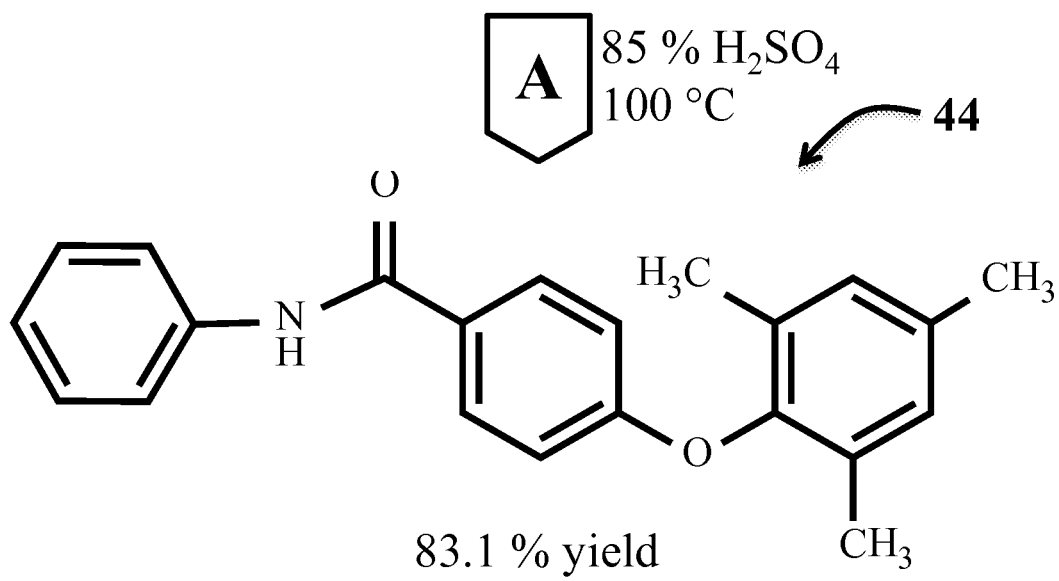
FIG. 4 illustrates a schematic representation of the Beckmann rearrangement of a first isomer product from the reaction of FIG. 3.
Figure 5:
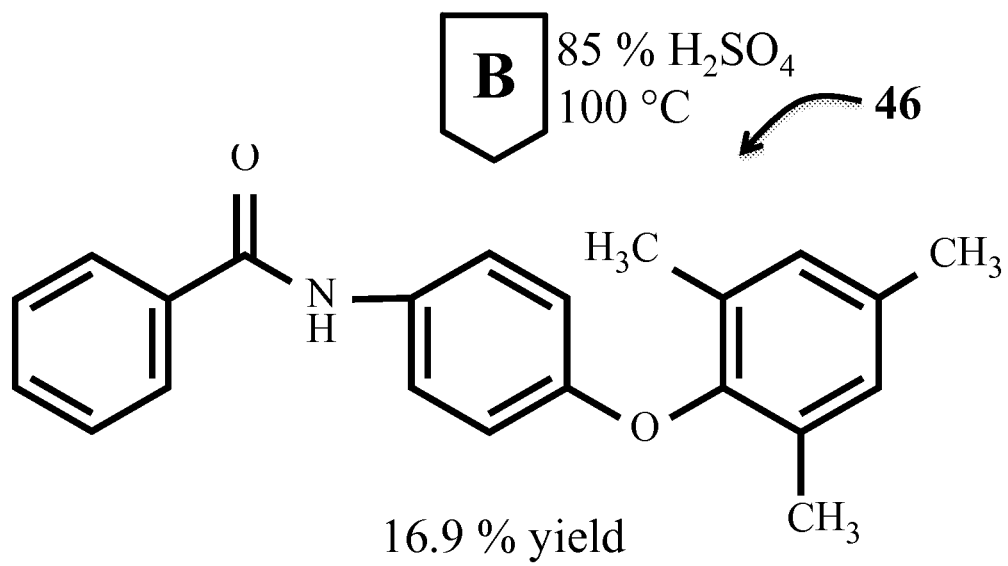
FIG. 5 illustrates a schematic representation of the Beckmann rearrangement of a second isomer product from the reaction of FIG. 3
Figure 6A:
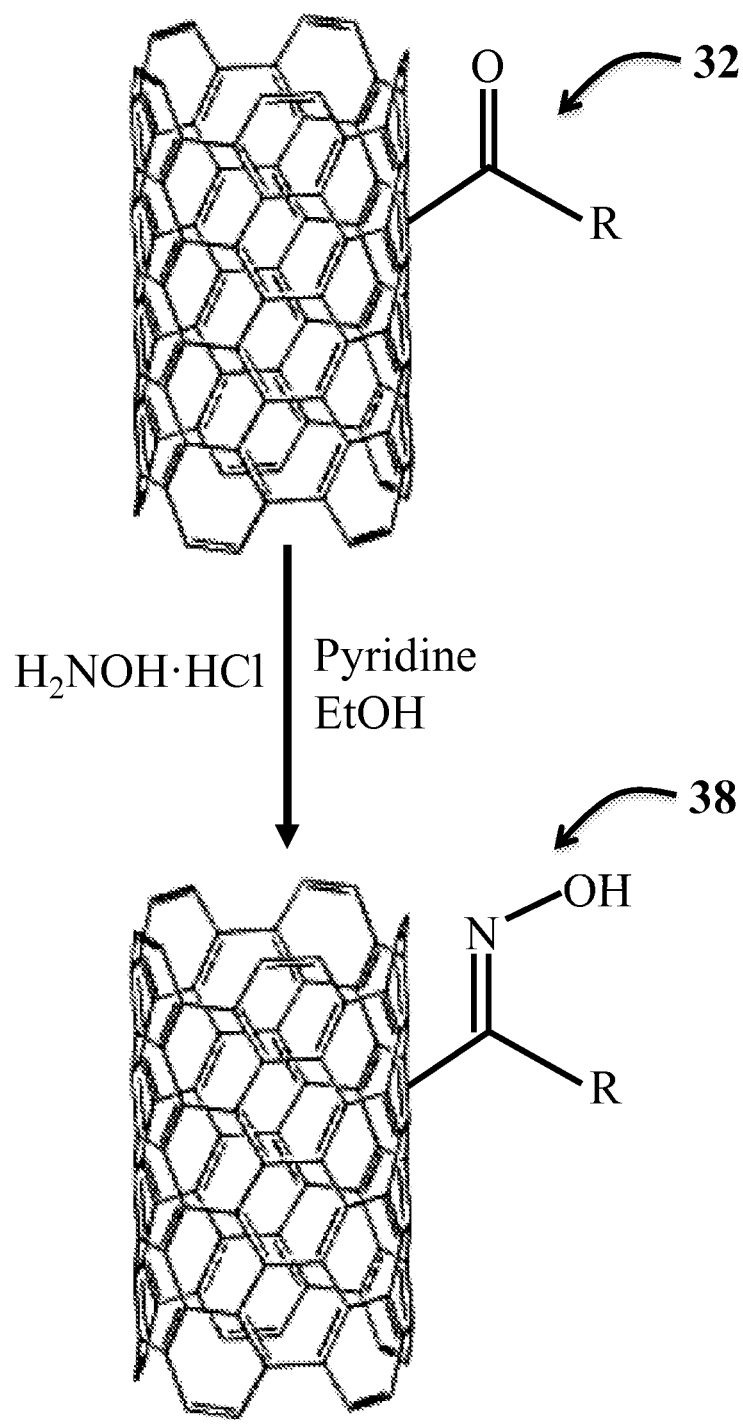
FIGS. 6A-6B illustrates a schematic representation of a chemical reaction between a CNT and hydroxylamine hydrochloride with Beckmann rearrangement of the oxime group.
Figure 6B:
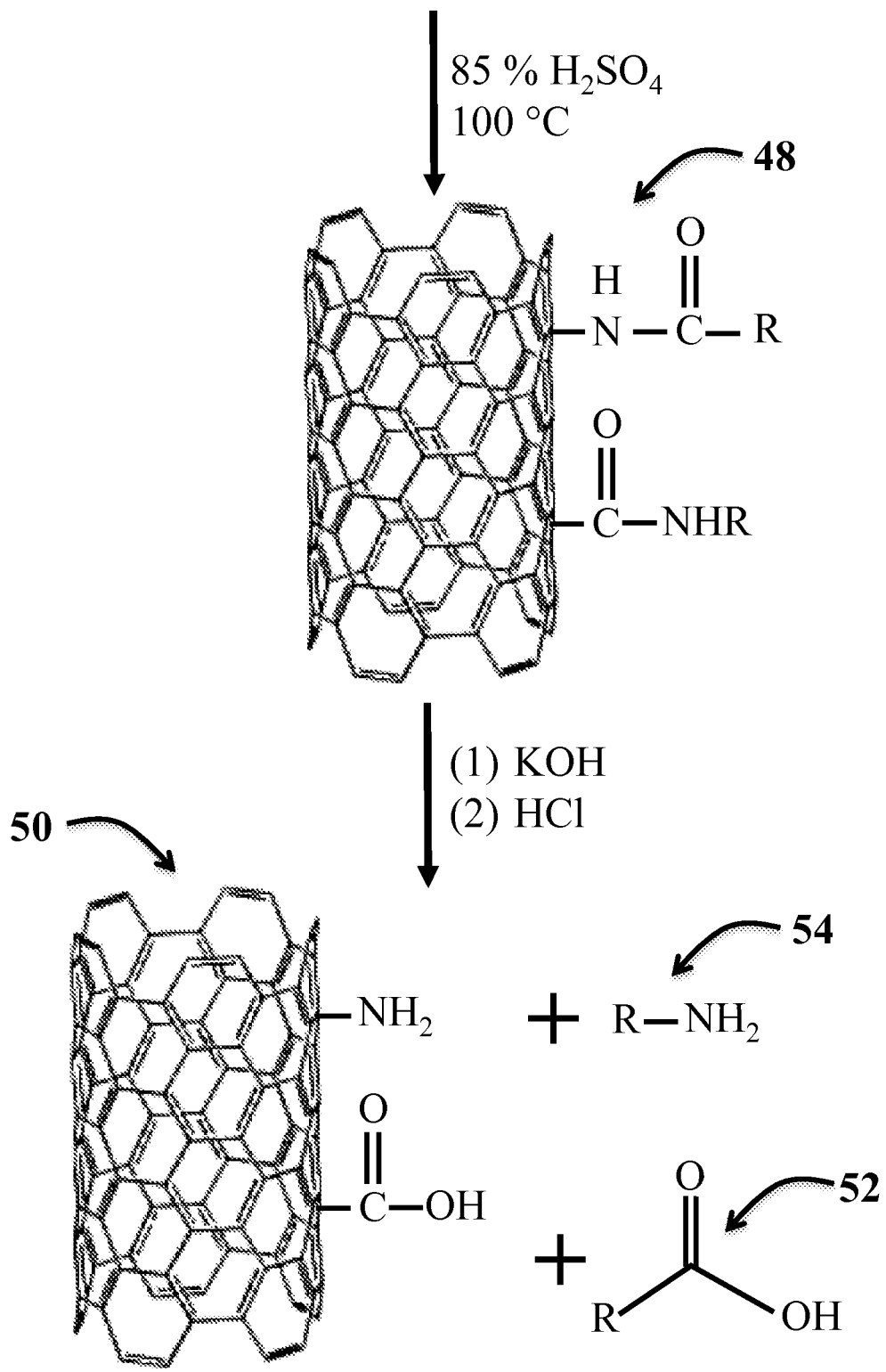

FIG. 2 is a flowchart further illustrating the Beckmann Rearrangement 26, with exemplary schemes as applied to a model compound (2,4,6-trimethylphenoxy)benzophenone in FIGS. 3-5 and to CNT in FIGS. 6A and 6B. In Block 28, the compound, whether 4-(2,4,6-trimethylphenoxy)benzophenone 30 of FIG. 3 or keto-carbonyl grafted CNT 32 of FIG. 6A from the reaction noted above with respect to FIG. 1) is reacted with hydroxylamine hydrochloride in pyridine/ethanol at an elevated temperature (for example, 90° C.). With not wishing to be bound by theory, it is believed that when an unsymmetrical ketoxime is involved, the Beckman Rearrangement is expected to form two structural isomers in the amide product. Accordingly, and as shown in FIG. 3, 4-(2,4,6-trimethylphenoxy)benzophenone 30 reacts with hydroxylamine hydrochloride to afford two oxime isomers 34, 36. Otherwise, and if a symmetric ketoxime is involved, then a single ketoxime-functional CNT product is formed, such as oxime-CNT 38 of FIG. 6A.

If desired, the products 34 (FIG. 3), 36 (FIG. 3), 38 (FIG. 6A) may be collected under filtration and dried (Optional Block 40), and before undergoing molecular rearrangement (Block 42) in a hot acid solution to form corresponding aromatic amide products 44 (FIG. 4), 46 (FIG. 5), 48 (FIG. 6B). The relative yield of a first product 44 (FIG. 4) and a second product 46 (FIG. 5) may be, for example, 83.1% to 16.9%. The degree of functionalization of the amide-CNT 48 (FIG. 6B) may be, for example, 1.3 atoms per 100 carbon atoms.

Figure 8:
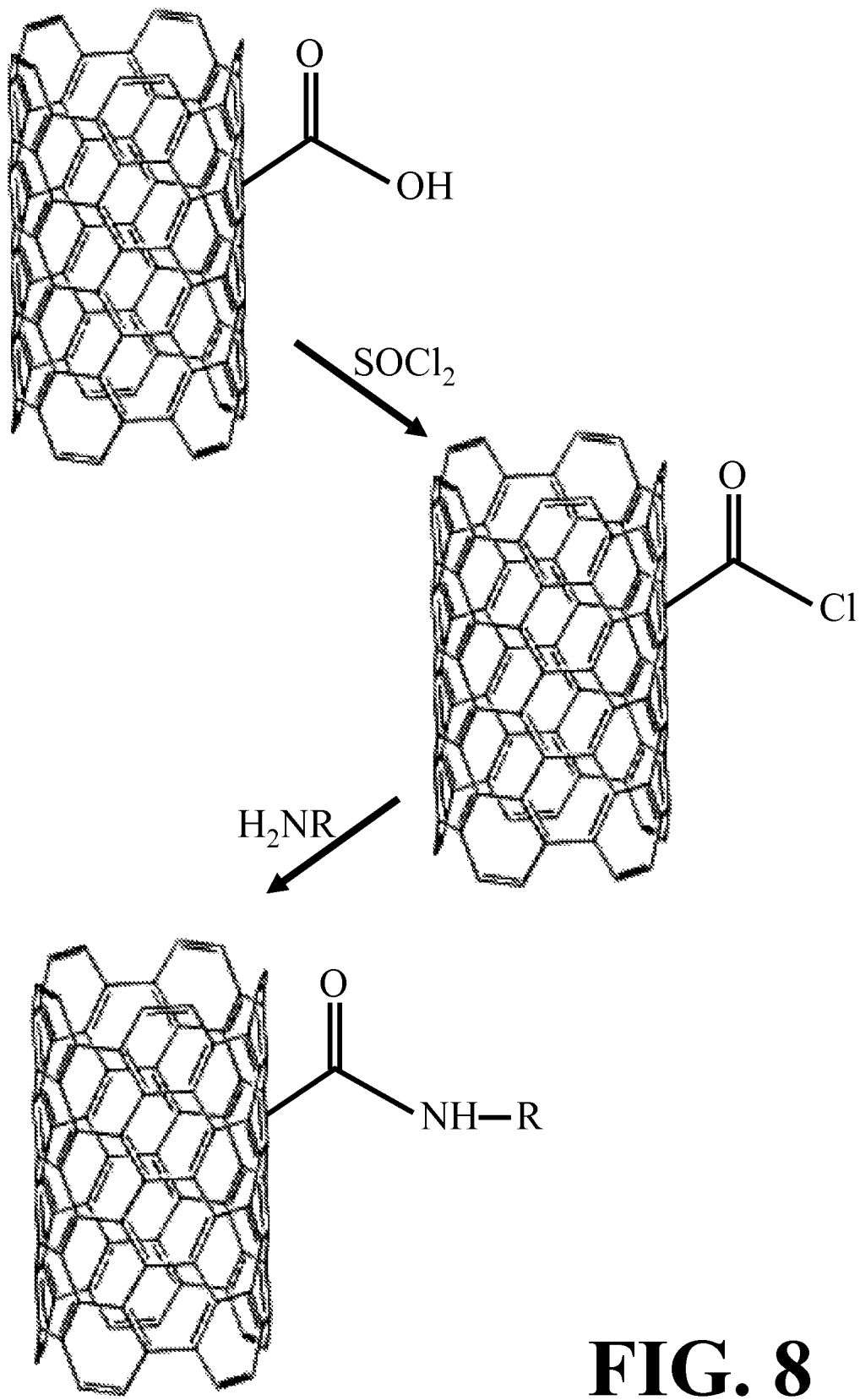
FIG. 8 illustrates a schematic representation of a convention chemical reaction for functionalizing a CNT.
Figure 9:
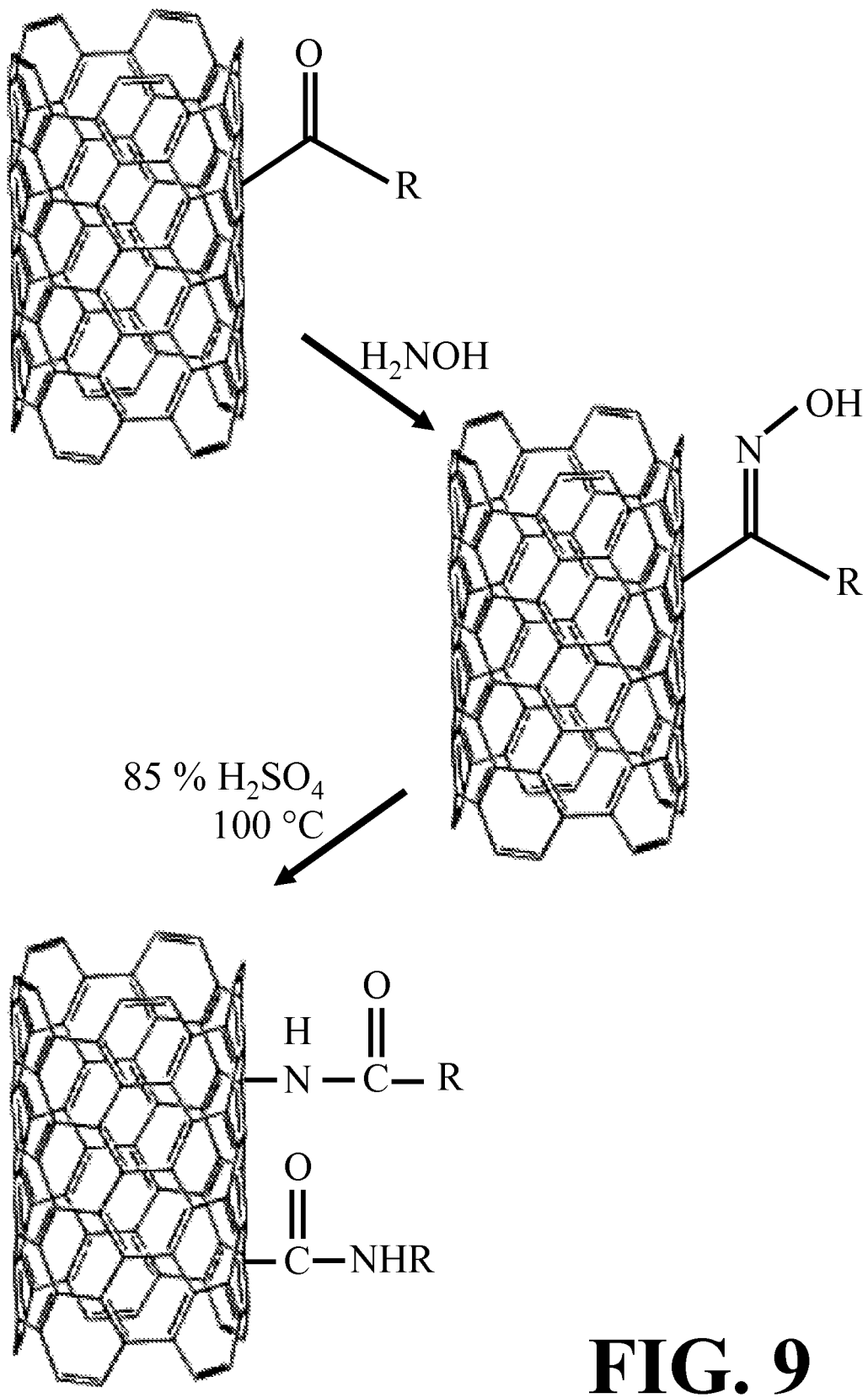
FIG. 9 illustrates a schematic representation of a chemical reaction, according to another embodiment of the present invention, between a CNT and hydroxylamine hydrochloride with Beckmann rearrangement of the oxime group It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

There are two isomeric forms of secondary amide moieties bonded to graphene surfaces of CNTs or CNFs, including $C_{graphene}$—C bond or a direct $C_{graphene-N}$ bond and corresponding to C-amide and N-amide, respectively. Conventional synthesis methods, illustrated in FIG. 8, invariably produce C-amide functionalized CNTs and CNFs. However, synthesis according to embodiments of the present invention, and as shown in FIG. 9, provides a near-quantitative yield of N-amide (98%) or mixture of N-amide (ranging from 72% to 86%) and C-amide (ranging from 14% to 28%) functionalized CNTs and CNFs, depending on the nature of R group in the starting keto-functionalized carbon nanomaterials.

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLE 1

Confirmation of Functionalized Amide-CNT

Functionalization of the amide-CNT 48 (FIG. 6B) was confirmed by comparing the FT-IR spectra of corresponding products, generally designated as keto-CNT. The corresponding products included Oxime-CNT-R and Amide-CNT-R, wherein R may be one compound selected from the group illustrated in FIGS. 7A-7C [4-(2,4,6-trimethylphenoxy)benzoyl ("TMPB"); 1-pyrene; and pentyl, respectively].

When R is TMPB, the corresponding Keto-CNT-R showed a ketone-carbonyl characteristic peak at 1664 $cm^{-1}$, which is absent in the resulting Oxime-CNT-R having characteristic CN and N—O stretches at 1604 $cm^{-1}$ and 996 $cm^{-1}$, respectively. After rearrangement, the amide-carbonyl peak at 1647 $cm^{-1}$ and associated N—H stretch at 3321 $cm^{-1}$ appeared in the Amide-CNT-R spectrum.

To determine the ratio of these isomers, Amide-CNT-R was hydrolyzed in potassium hydroxide/ethanol under refluxing condition. After work-up, a mixture of the hydrolysis product 50, carboxylic acid 52, and amine 54 in solution was separated from the solid product and injected into a GC-MS instrument for analysis. GC peak locations were compared with those of known compounds. The ratios of carboxylic acid 52 and amine 54 were obtained by integration of both GC peak areas.

The hydrolysis of Amide-CNT-R resulted in 98% of 4-(1,3,5-trimethylphenoxy)benzoic acid 52 and only 2% of 4-(1,3,5-trimethylphenoxy)aniline 54. It is believed that the carboxylic acid 52 is dominant because anti-Oxime-CNT is encountering much less steric hindrance than its syn-counterpart and the predominant presence of syn-configuration of the ketoxime moiety as the result of the OH group moving away from the nonpolar graphene surface. The significant implication of this observation is that despite being part of a bulky graphene system, the surface $sp^2$ carbon may be an active participant in the molecular rearrangement of the pendant.

EXAMPLE 2

4-(2,4,6-Trimethylphenoxy)benzonitrile 2,4,6-Trimethylphenol (6.00 g, 44.1 mmol), 4-fluorobenzonitrile (5.34 g, 44.1 mmol), potassium carbonate (7.30 g, 52.8 mmol), a mixture of NMP (100 mL), and toluene (60 mL) were placed into a 250 mL three-necked, round-bottomed flask equipped with a magnetic stir-bar, nitrogen inlet, and a condenser. The reaction mixture was then heated and maintained at a temperature of about 140° C. for 8 hr under nitrogen. The dark solution was filtered while warm, and the filtrate was poured into distilled water containing 5% hydrochloric acid. The solution was separated into organic and aqueous layers. The organic layer was diluted with dichloromethane and separated. The solvent was removed from the dichloromethane extract to dryness. The resulting light brown oily residue was freeze-dried to afford 10.1 g (97% yield):

Analytical calculation for $C_{16}H_{15}NO$: C, 80.98%; H, 6.37%; N, 5.90%; 0, 6.74%.

Found: C, 80.31%; H, 6.37%; N, 5.75%; 0, 6.46%. FT-IR (KBr, $cm^{-1}$): 2226 (CN stretch).

Mass spectrum (m/e): 237 ($M^+$ 100% relative abundance), 222, 204, 194. $^1H$ NMR ($CDCl_3$, ppm) δ 2.05 (s, 6H, $CH_3$), 2.30 (s, 3H, $CH_3$), 6.81-6.84 (d, 2H, Ar), 6.91 (s, 2H, Ar), 7.53-7.56 (d, 2H, Ar). $^{13}C$ NMR ($CDCl_3$, ppm) δ 16.10, 20.79, 115.48, 129.07, 129.15, 129.88, 130.48, 134.25, 147.84, 150.03, 161.44.

EXAMPLE 3

4-(2,4,6-Trimethylphenoxy)benzoic acid 4-(2,4,6-Trimethylphenoxy)benzonitrile (10.0 g, 42.0 mmol), and phosphoric acid (100 mL) were placed into a 250 mL three-necked round-bottomed flask equipped with a magnetic stir-bar, nitrogen inlet, and a condenser. The reaction mixture was then heated and maintained at a temperature of about 150° C. for 8 hr. After cooling down to room temperature, the mixture was poured into distilled water containing 5% hydrochloric acid. The resulting precipitates were collected by suction filtration, air-dried, dissolved in warm heptane, and filtered. The filtrate was allowed to cool to room temperature to afford 4.5 g (42% yield) of white crystal: m.p. 236-238° C.

Analytical calculation for $C_{16}H_{16}O_3$: C, 74.98%; H, 6.29%; 0, 18.73%.

Found: C, 74.76%; H, 6.67%; 0, 18.56%. FT-IR (KBr, $cm^{-1}$): 1650 (C=O stretch), 3385 (O—H stretch).

Mass spectrum (m/e): 256 ($M^+$, 100% relative abundance), 255. $^1H$ NMR (DMSO-$d_6$, ppm) δ 2.00 (s, 6H, $CH_3$), 2.67 (s, 3H, $CH_3$), 6.74-6.77 (d, 2H, Ar), 6.98 (s, 2H, Ar), 7.82-7.86 (d, 2H, Ar). $^{13}C$ NMR (DMSO-$d_6$, ppm) δ 15.80, 20.41, 113.80, 127.65, 129.69, 129.81, 130.12, 134.47, 147.95, 159.95, 167.06.

EXAMPLE 4

4-(2,4,6-Trimethylphenoxy)benzophenone 2,4,6-Trimethylphenol (2.72 g, 20.0 mmol), 4-fluorobenzophenone (4.00 g, 20.0 mmol), potassium carbonate (3.32 g, 24.0 mmol), a mixture of DMAc (40 mL), and toluene (10 mL) were placed into a 250 mL three-necked, round-bottomed flask equipped with a magnetic stir-bar, nitrogen inlet, and a Dean-Stark trap with a condenser. The reaction mixture was then heated and maintained at a temperature of about 140° C. for 6 hr with nitrogen flow. The brown mixture was filtered while warm, and the filtrate was poured into distilled water containing 5% hydrochloric acid. The solution was phase-separated into an organic layer and an aqueous layer. The organic layer was diluted with dichloromethane and separated. The solvent was removed from the $CH_2Cl_2$ extract to dryness to afford 6.00 g (95%) of a light brown oily residue, which solidified upon standing at room temperature: m.p. 52-54° C.

Analytical calculation for $C_{22}H_{29}O_2$: C, 83.52%; H, 6.37%; 0, 10.11%.

Found: C, 83.15%; H, 6.51%; 0, 10.52%. FT-IR (KBr, $cm^{-1}$): 3058, 2919, 2859, 1655 (C=O), 1597, 1500, 1307, 1278, 1235, 1165, 847, 700.

Mass spectrum (m/z): 316 (Ml, 100% relative abundance), 239, 105, 91, 77.

$^1H$ NMR ($CDCl_3$, ppm) δ 2.09 (s, 6H, $CH_3$), 2.31 (s, 31-1, $CH_3$), 6.82-6.84 (d, 21-1, Ar), 6.92 (s, 2H, Ar—H), 7.44-7.48 (t, 2H, Ar—H), 7.54-7.58 (t, 1H, Ar—H), 7.75-7.80 (overlapped d, 4H, Ar—H). $^{13}C$ NMR ($CDCl_3$, ppm) δ 16.16, 20.76, 114.28, 128.15, 129.69, 129.73, 130.63, 130.73, 131.93, 132.70, 134.98, 138.08, 148.22, 161.67, 195.46.

EXAMPLE 5

4-(2,4,6-Trimethylphenoxy)benzophenone oxime 4-(2,4,6-Trimethylphenoxy)benzophenone 30 (FIG. 3) (3.16 g 10 mmol), hydroxylamine hydrochloride (3.50 g, 50 mmol), pyridine (20 mL), and ethanol (50 mL) were placed into a 250 mL three-necked, round-bottomed flask equipped with a magnetic stir-bar, nitrogen inlet. The reaction mixture was then heated and maintained at a temperature of about 90° C. for 8 hr with nitrogen flow. Most solvents were removed by a rotavap, water (100 mL) was added, and the resulting mixture extracted with ethyl acetate. The organic layer was separated, washed with water 3 times, and finally dried over magnesium sulfate. After filtration to remove MgSO$_4$, the filtrate was evaporated to dryness and dried in oven at 100° C. overnight to afford 3.15 g (99%) of white solid, m.p. 175.1-175.4° C. FT-IR (KBr, cm$^{-1}$): 3228 (Br, OH), 3060, 2916, 1601, 1507, 1479, 1328, 1201, 994, 835, 765, 692.

EXAMPLE 6

4-(2,4,6-Trimethylphenoxy)-N-phenylbenzamide and N-[4-(2,4,6-Trimethylphenyoxy)phenyl]benzamide 4-(2,4,6-Trimethylphenoxy)benzophenone oxime (0.50 g, 1.5 mmol) and sulfuric acid (10 mL, 85%) were added into a 50 mL three-necked, round-bottomed flask equipped with a magnetic stir-bar and nitrogen inlet. The mixture was heated at a temperature of about 100° C. for 1 hr. After cooling down to room temperature, the resulting mixture was poured into ice. The precipitate was collected to afford 0.43 g (86%) of white powder. FT-IR (KBr, cm$^{-1}$): 3319 (amide, N—H), 3059, 2918, 2857, 1649 (amide, C=O), 1599, 1503, 1440, 1321, 1241, 1167, 751, 691.

EXAMPLE 7

Functionalization of CNTs with 4-(2,4,6-trimethylphenoxy)benzoic acid 4-(2,4,6-Trimethylphenoxy)benzoic acid (0.50 g, 1.95 mmol), CNT (0.50 g of Graphistrengh® C100, Arkema, Colombes Cedex, France), and poly(phosphoric acid) (83% assay, 40 g) were place into a 250 mL resin flask equipped with a high torque mechanical stirrer and nitrogen inlet and outlet and stirred with dried nitrogen purging at 130° C. for 24 hr. P$_2$O$_5$ (10 g) was then added in one portion. The initially dark mixture became dark brown after 24 hr. The temperature was maintained at 130° C. for 72 hr. After cooling down to room temperature, water was added to the reaction vessel and the content was poured into a beaker of water (about 1 L). The resulting precipitates were collected, washed with (1) diluted ammonium hydroxide; (2) Soxhlet-extracted with water for three days and (3) with methanol for three days; (4) and dried over phosphorus pentoxide under reduced pressure at 100° C. for 72 hr to give 0.60 g (95%) of dark brown solid. FT-IR (KBr, cm$^{-1}$): 3435, 2922, 2856, 1659 (keto C=O), 1594, 1389, 1230, 1152, 913.

EXAMPLE 8

Functionalization of MWCNTs with 1-pyrenecarboxylic acid

Figure 7A:
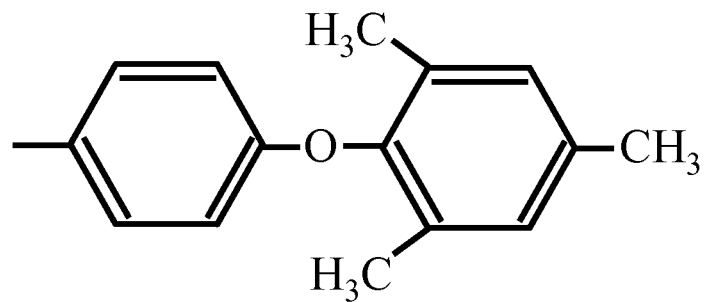
FIGS. 7A-7C illustrates exemplary R groups of the products in FIGS. 6A-6B.
Figure 7B:
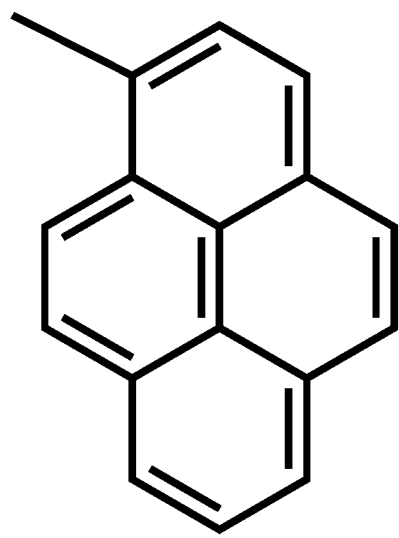

Keto-CNT-Re (FIG. 6B), wherein R is the 1-pyrene of FIG. 7B, was synthesized from 1-pyrenecarboxylic acid (0.50 g, 2.03 mmol) and MWCNT (0.50 g) using the same procedure as was described in Example 7 to afford 0.57 g (91% yield) of dark brown solid.

Analytical calculation for $C_{122.1}H_{11.7}O_{1.3}$ (based on the assumption that for every 100 carbon, there are 1.3 1-pyrenecarbonyl groups attached): C, 97.82%; H, 0.79%; 0, 1.39%.

Found: C, 97.56%; H, 0.88%; 0, 1.42%. FT-IR (KBr, cm$^{-1}$): 3036, 1641 (C=O), 1512, 1277, 840.

EXAMPLE 9

Functionalization of MWNTs with 1-hexanoic acid

Figure 7C:

Keto-CNT-R (FIG. 6B), wherein R is the pentyl of FIG. 7C, was synthesized from 1-hexanoic acid (0.50 g, 4.31 mmol) and MWCNT (0.50 g) using the same procedure as was described in Example 7 to afford 0.49 g (88%) of dark brown solid.

Analytical calculation for $C_{107.8}H_{14.3}O_{1.3}$ (based on the assumption that for every 100 carbon, there are 1.3 hexanoyl groups attached): C, 98.32%; H, 1.30%; 0, 1.56%.

Found: C, 97.94%; H, 1.26%; 0, 1.63%. FT-IR (KBr, cm$^{-1}$): 2928, 2863, 1648, 1458, 1202.

EXAMPLE 10

Conversion of Keto-CNT-R to Oxime-CNT-R

Keto-CNT-R (FIG. 6B), wherein R is the TMPB of FIG. 7A, keto-carbonyl grafted CNT 32 (FIG. 6A) (0.50 g), hydroxylamine hydrochloride (2.00 g, 28.6 mmol), pyridine (20 mL), and ethanol (1000 mL) were added into a 250 mL three-necked, round-bottomed flask equipped with a magnetic stir-bar, nitrogen inlet. The reaction mixture was then sonicated for 1 hr and heated to a temperature of about 90° C. for 2 d. The solution was then poured into water. The black precipitate was collected by filtration, washed with ethanol, and dried in an oven at 100° C. overnight to afford 0.51 g (99%) of black powder. FT-IR (KBr, cm$^{-1}$): 3420 (oxime O—H), 2920, 1501, 1604 (oxime C=N), 1228, 1163, 996 (oxime N-0).

EXAMPLE 11

Conversion of Oxime-CNT-R to Amide-CNT-R

Oxime-CNT-R (0.20 g), wherein R is the TMPB of FIG. 7A, and sulfuric acid (10 mL) were placed into a 50 mL three-necked, round-bottomed flask equipped with a magnetic stir-bar and nitrogen inlet. The reaction mixture was then sonicated for 1 hr and heated at 100° C. for 1 d. The solution was then poured into ice water. The black precipitate was collected by filtration, washed in water, and dried in oven at 100° C. overnight to afford 0.18 g (90%) of black powder. FT-IR (KBr, cm$^{-1}$): 3321 (amide N—H), 2920, 1647 (amide C=O), 1601, 1499, 1324, 1227, 1154.

EXAMPLE 12

Hydrolysis of Amide-CNT-R

Amide-CNT-R (0.20 g), wherein R is the TMPB of FIG. 7A, and ethanol (10 mL) were placed into a 50 mL three-necked, round-bottomed flask equipped with a magnetic stir-bar and nitrogen inlet. The reaction mixture was then sonicated for 1 hr and potassium hydroxide (2.0 g, 3.6 mmol) was added. The mixture was heated under refluxing for 1 d and then poured into water in a beaker. Dilute HCl solution (2N) was added until pH was about 6-7, followed by addition of ethyl acetate, and the resulting heterogeneous mixture was magnetically stirred. Upon standing, the top organic layer of mixture was separated from the lower aqueous phase with solid particles at the bottom of the beaker and dried over sodium sulfate. After filtration, the solid was dried to afford 0.12 g (75%) of black power (CNT-R', where R' is NH$_2$ or COOH). The ethyl acetate extract of the filtrate was rotary-evaporated to dryness to afford 0.03 g (76%) of white crystalline products included carboxylic acid 52 (FIG. 6B) and amine 54 (FIG. 6B), which were then dissolved in acetonitrile and injected into GC-MS sample port for quantitative identification.

EXAMPLE 13

Hydrolysis of Amide-CNT-R

Hydrolysis of Amide-CNT-R, wherein R is the 1-pyrene of FIG. 7B, was performed using the same procedure as was described in Example 12 using Amide-CNT-R (0.16 g), ethanol (10 mL), and potassium hydroxide (2.0 g, 3.6 mmol) to afford 0.09 g (82%) of black power (CNT-R', where R' is $NH_2$ or COOH), and the ethyl acetate extract filtrate was rotary-evaporated to dryness to afford 0.03 g (75%) of yellow crystals (mixture of carboxylic acid 52 and amine 54), which were then dissolved in acetonitrile and injected into GC-MS sample port for identification and quantification.

EXAMPLE 14

Hydrolysis of Amide-CNT-R

Hydrolysis of Amide-CNT-R, wherein R is the pentyl of FIG. 7C, was performed using the same procedure as was described in Example 12 using Amide-CNT-R (0.16 g), ethanol (10 mL), and potassium hydroxide (2.0 g, 3.6 mmol) to afford 0.10 g (78%) of black power (MWCNT-R', where R' is $NH_2$ or COOH), and the ethyl acetate extract was rotary-evaporated to remove the solvent to afford 0.02 g (76%) of a colorless liquid (carboxylic acid 52 and amine 54), which was then dissolved in acetonitrile and injected into GC-MS sample port for identification and quantification.

EXAMPLE 15

Hydrolysis of Amide-CNT-R

GC-MS analysis and associated plots were obtained on a CP-3800 Gas Chromatographer and TQ-Mass Spectrometer (Varian Medical Systems, Inc., Palo Alto, Calif.). A "25 min" method was used for all the samples, wherein operational parameters included an injector temperature of 250° C.; column helium flow rate of 1.0 mL/min; and flame ionization detector (FID) temperature of 250° C. The column oven temperature was held at 50° C. for 0.5 min after each analyte had been injected. The oven temperature was then raised, at the rate of 20° C./min to 300° C./min for 12.5 min and held at 300° C. for 12 min.

The carboxylic acid 52 (FIG. 6B) and amine 54 (FIG. 6A) reference compounds were specially synthesized. Other reference compounds included 1-aminopentane (1-pentylamine), 1-hexanoic acid, 1-aminopyrene, and 1-pyrenecarboxylic acid. The reference compounds, 4-(1,3,5-trimethoxyphenoxy)benzoic acid and 4-(1,3,5-trimethoxyphenoxy)aniline were prepared as described in Example 3 and Example 16, respectively.

TABLE 1

| R group designation | N-amide (%) | C-amide (%) |
| --- | --- | --- |
| TMPB (FIG. 7A) | 98 | 2 |
| 1-pyrene (FIG. 7B) | 86 | 14 |
| pentyl (FIG. 7C) | 100 | 0 |

EXAMPLE 16

Synthesis of 4-(1,3,5-trimethoxyphenoxy)aniline for GC-MS analysis 2,4,6-Trimethylphenol (7.50 g, 55.0 mmol), 4-fluoronitrobenzene (7.10 g, 50.0 mmol), potassium carbonate (7.60 g, 55.0 mmol), and N,N'-dimethylformamide (100 mL) were placed into a 250 mL three-necked, round-bottomed flask equipped with a magnetic stir-bar and nitrogen inlet. The reaction mixture was agitated at room temperature for 24 hr with nitrogen flow. The brown mixture was filtered, and the filtrate was poured into distilled water. The solution phase-separated into an organic layer and an aqueous layer. The organic layer was diluted with ethyl acetate and separated. The solvent was removed by rotary evaporation. The semi-solid was purified by a column (basic alumina) chromatography with a 1:9/ethyl acetate:hexane mixture as eluent to eventually afford 7.31 g (58.4%) of 1,3,5-trimethyl-2-(4-nitrophenoxy)benzene as a colorless liquid, which, upon standing in a refrigerator, was solidified to a light yellow solid m.p. 46-48° C.

Analytical calculation for $C_{15}H_{15}NO_3$: C, 70.02%; H, 5.88%; N, 5.44.

Found: C, 69.87%; H, 5.78%; N, 5.45%.

Mass spectrum (m/z): 257. $^1H$ NMR (DMSO-$d_6$, ppm) δ: 1.98 (s, 6H, $CH_3$), 2.24 (s, 3H, $CH_3$), 6.88-6.89 (d, 2H, Ar—H), 6.97 (s, 2H, Ar—H), 8.17-8.19 (d, 2H, Ar—H). $^{13}C$ NMR (DMSO-$d_6$, ppm) δ: 15.58, 22.28, 114.9, 126.33, 128.6, 129.8, 135.1, 141.7, 147.5, 162.5.

1,3,5-Trimethyl-2-(4-nitrophenoxy)benzene (4.0 g, 15.6 mmol) was then dissolved in ethyl acetate (100 mL) and palladium on activated carbon (0.20 g) was placed in a hydrogenation bottle. The bottle was tightly secured on a Parr hydrogenation apparatus, flushed four times with hydrogen gas, and pressurized to 60 psi. After agitation at room temperature for 12 hr under the hydrogen pressure of 60 psi, the solution was filtered through Celite. The filter cake was washed with ethyl acetate, and the filtrate was evaporated to dryness on a rotary evaporator and the resulting crude product was recrystallized from ethanol/water to afford 3.25 g (92%) of light brown crystals: m.p. 94-95° C.

Analytical calculation for $C_{15}H_{17}NO$: C, 79.26%, H, 7.54%, N, 6.16%,

Found: C, 79.19%, H, 7.55%, N, 5.95%.

Mass spectrum (m/z): 227. $^1H$ NMR (DMSO-$d_6$, δ in ppm): 1.99 (s, 6H, $CH_3$), 2.22 (s, 3H, $CH_3$), 4.63 (s, 2H, $NH_2$), 6.39-6.41 (d, 2H, Ar—H), 6.45-6.48 (d, 2H, Ar—H), 6.89 (s, 2H, Ar—H).

EXAMPLE 17

Table 2, below, summarizes a degree of functionalization determined based on thermogravimetric analysis and elemental analysis results of pristine and functionalized MWCNTs. The superscript "a" in Table 2 indicates a value less than the detection limit. The subscript "b" in Table 2 indicates the theoretical calculation of C %, H %, and N % were based on the assumption that for every 1000 carbons there are 13 (i.e., degree of functionality or τ=1.3 at. %, based on reported TGA and elemental results) functional groups ($C_nH_mN_pO_q$) attached from the following equation:

$$C \% = \frac{(100 + \tau*n)*12.01}{100*12.01 + \tau(12.01n + 1.01m + 14.01p + 16.00q)};$$

$$H \% = \frac{\tau*m*1.01}{100*12.01 + \tau(12.01n + 1.01m + 14.01p + 16.00q)};$$

$$N \% = \frac{\tau*p*14.01}{100*12.01 + \tau(12.01n + 1.01m + 14.01p + 16.00q)}; \text{ and}$$

$$O \% = \frac{\tau*q*16.00}{100*12.01 + \tau(12.01n + 1.01m + 14.01p + 16.00q)},$$

where the subscripts n, m, p, and q are the numbers of carbon, hydrogen, nitrogen, and oxygen, respectively, in one functional group. The atomic weights of carbon, hydrogen, nitrogen, and oxygen are 12.01 g/mol, 1.01 g/mol, 14.01 g/mol, and 16.00 g/mol, respectively.

Returning again to Table 2, the superscript "c" indicates a CNT content calculated as follows:

$$\text{CNT Content} = \frac{100*12.01}{100*12.01 + \tau(12.01 + 16 + 1.01*15 + 2*16.00)}.$$

The superscript "d" in Table 2 indicates a residual weight percent at a temperature ranging from 550° C. to 600° C. from TGA thermograms in air.

TABLE 2

| Sample No. | DF τ | CNT Content (%) Calculated | Found[d] | Elemental Analysis | C (%) | H (%) | N (%) |
|---|---|---|---|---|---|---|---|
| MWCNT | 0 | 100 | 95.10 | Calculated | 100 | 0 | 0 |
|  |  |  |  | Found | 95.10 | 0.40 | <0.1[a] |
| Keto-CNT-TMPB | 1.3 | 79.4[c] | 79.4 | Calculated for $C_{120.8}H_{19.5}O_{2.6}$[b] | 95.94 | 1.30 | 0 |
|  |  |  |  | Found | 94.67 | 1.26 | <0.1[a] |
| Keto-CNT-l-pyrene | 1.3 | 80.1[c] | 80.1 | Calculated for $C_{122.1}H_{11.7}O_{1.3}$[b] | 97.82 | 0.79 | 0 |
|  |  |  |  | Found | 97.56 | 0.88 | <0.1[a] |
| Keto-CNT-pentyl | 1.3 | 90.3[c] | 90.3 | Calculated for $C_{107.8}H_{14.3}O_{1.3}$[b] | 97.35 | 1.09 | 0 |
|  |  |  |  | Found | 97.22 | 1.12 | <0.1[a] |
| Oxime-CNT-TMPB | 1.3 | 78.4[c] | 78.2 | Calculated for[b] $C_{120.8}H_{20.8}N_{1.3}O_{2.6}$ | 94.72 | 1.37 | 1.19 |
|  |  |  |  | Found | 94.65 | 1.39 | 1.22 |
| Oxime-CNT-pyrene | 1.3 | 79.1[c] | 79.0 | Calculated for[b] $C_{122.1}H_{13.0}N_{1.3}O_{1.3}$ | 96.57 | 0.86 | 1.20 |
|  |  |  |  | Found | 96.43 | 0.89 | 1.24 |
| Oxime-CNT-pentyl | 1.3 | 89.0[c] | 89.7 | Calculated for[b] $C_{107.8}H_{15.6}N_{1.3}O_{1.3}$ | 95.94 | 1.17 | 1.35 |
|  |  |  |  | Found | 95.81 | 1.13 | 1.32 |
| Amide-CNT-TMPB | 1.3 | 78.4[c] | 78.2 | Calculated for[b] $C_{120.8}H_{20.8}N_{1.3}O_{2.6}$ | 94.72 | 1.37 | 1.19 |
|  |  |  |  | Found | 94.65 | 1.41 | 1.17 |
| Amide-CNT-pyrene | 1.3 | 79.1[c] | 79.2 | Calculated for[b] $C_{122.1}H_{13.0}N_{1.3}O_{1.3}$ | 96.57 | 0.86 | 1.20 |
|  |  |  |  | Found | 96.43 | 0.82 | 1.15 |
| Amide-CNT-pentyl | 1.3 | 89.0[c] | 89.6 | Calculated for[b] $C_{107.8}H_{15.6}N_{1.3}O_{1.3}$ | 95.94 | 1.17 | 1.35 |
|  |  |  |  | Found | 96.10 | 1.15 | 1.32 |

As described in detail herein, chemical attachment of ketone-oxime (or simply ketoxime) moieties onto the surfaces of multi wall carbon nanotubes (MWCNT) and carbon nanofibers (CNF) via sequential Friedel-Crafts acylation in polyphosphoric acid and condensation with hydroxylamine is described according to various embodiments of the present invention. Additional embodiments of the present invention are directed to methods to obtain one-dimensional carbon nanomaterials with directly bound secondary amide (—CONHR) and primary amine (—NH$_2$) via a tandem application of Beckmann Rearrangement in aqueous sulfuric acid and alkaline hydrolysis reaction.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A functionalized nanomaterial comprising:
   a nanomaterial comprising a carbon nanotube or a carbon nanofiber;
   at least one ketoxime group coupled to a first location on the nanomaterial; and
   at least one amide group coupled to a second location on the nanomaterial.

2. A method of synthesizing the functionalized nanomaterial of claim 1, the method comprising:
   converting a plurality of keto-carbonyl groups to a plurality of ketoxime groups, the plurality of keto-carbonyl groups being coupled to the nanomaterial; and
   rearranging, with a Beckmann Rearrangement, a portion of the plurality of ketoxime groups to the at least one amide group.

3. The method of claim 2, further comprising:
   grafting, with a Friedel-Crafts acylation, the plurality of keto-carbonyl groups onto the nanomaterial.

4. The method of claim 2, wherein converting the plurality of the keto-carbonyl groups to the at least one ketoxime group includes reacting at least one keto-carbonyl group with hydroxylamine hydrochloride in pyridine and ethanol.

5. The method of claim 2, wherein rearranging with the Beckmann Rearrangement includes treating the plurality of ketoxime groups with a heated acid solution.

6. A functionalized nanomaterial comprising:
   a nanomaterial comprising a carbon nanotube or a carbon nanofiber; and
   at least one ketoxime group coupled to the nanomaterial.

7. The functionalized nanomaterial of claim 6, wherein the nanomaterial has a degree of functionalization ranging from about 1% to about 3%.

8. A functionalized nanomaterial comprising:
   a nanomaterial comprising a carbon nanotube or a carbon nanofiber; and at least one amide group coupled to the nanomaterial via a N-amide coupling.

9. The functionalized nanomaterial of claim 8, wherein the nanomaterial has a degree of functionalization ranging from about 1% to about 3%.

10. The functionalized nanomaterial of claim 8, further comprising a second amide group coupled to the nanomaterial via a C-amide coupling.

11. A method of synthesizing the functionalized nanomaterial of claim 8, the method comprising:
grafting, with a Friedel-Crafts acylation, at least one keto-carbonyl group onto a nanomaterial;
converting the at least one keto-carbonyl group to at least one ketoxime group to provide a ketoxime-functionalized nanomaterial; and
rearranging, with a Beckmann Rearrangement, the at least one ketoxime group to the at least one amide group coupled to the nanomaterial via the N-amide coupling.

12. The method of claim 11, wherein the Beckmann Rearrangement further provides a second amide group coupled to the nanomaterial via a C-amide coupling.

13. The functionalized nanomaterial of claim 1, wherein the nanomaterial has a degree of functionalization ranging from about 1% to about 3%.

14. A method of synthesizing the functionalized nanomaterial of claim 6, the method comprising:
grafting, with a Friedel-Crafts acylation, at least one keto-carbonyl group onto the nanomaterial;
converting the at least one keto-carbonyl group to the at least one ketoxime group.

15. The method of claim 14, wherein converting the at least one keto-carbonyl group to the at least one ketoxime group includes reacting the at least one keto-carbonyl group with hydroxylamine hydrochloride in pyridine and ethanol.

\* \* \* \* \*